US012194260B2

(12) United States Patent
Rosenberg et al.

(10) Patent No.: US 12,194,260 B2
(45) Date of Patent: Jan. 14, 2025

(54) IDENTIFYING THE STATE OF A BALLOON CATHETER

(71) Applicant: Biosense Webster (Israel) Ltd., Yokneam (IL)

(72) Inventors: Avigdor Rosenberg, Kiryat Tivon (IL); Eliran Guzi, Haifa (IL); Lior Zar, Poria Illit (IL); Alaa Zoubi, Sakhnin (IL); Ahmed Abdelaal, Mission Viejo, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 796 days.

(21) Appl. No.: 17/386,392

(22) Filed: Jul. 27, 2021

(65) Prior Publication Data
US 2023/0033654 A1    Feb. 2, 2023

(51) Int. Cl.
*A61M 25/10* (2013.01)
*A61B 5/283* (2021.01)
*A61B 18/14* (2006.01)

(52) U.S. Cl.
CPC ........ *A61M 25/10187* (2013.11); *A61B 5/283* (2021.01); *A61B 18/1492* (2013.01); *A61M 2205/3317* (2013.01)

(58) Field of Classification Search
CPC ...... A61M 25/10184; A61M 25/10187; A61M 25/10188; A61M 2205/3317; A61B 18/14; A61B 18/1492; A61B 2018/00214; A61B 2018/0022; A61B 2018/00267; A61B 2018/00351; A61B 2018/00875; A61B 17/00234; A61B 17/00557; A61B 2017/00243; A61B 5/065; A61B 5/28; A61B 5/282; A61B 5/283; A61B 5/287; A61B 5/6852; A61B 5/6853; A61B 5/6858; A61B 5/7435; A61B 2034/2051; A61B 2034/2061; A61B 2090/06; A61B 2090/061

See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker et al. |
| 5,944,022 A | 8/1999 | Nardella et al. |
| 5,983,126 A | 11/1999 | Wittkampf |
| 6,177,792 B1 | 1/2001 | Govari et al. |
| 6,690,963 B2 | 2/2004 | Ben-Haim et al. |
| 6,788,967 B2 | 9/2004 | Ben-Haim et al. |
| 7,536,218 B2 | 5/2009 | Govari et al. |

(Continued)

OTHER PUBLICATIONS

Extended European Search Report dated Dec. 22, 2022, from corresponding European Application No. 22186837.5.

*Primary Examiner* — Robert A Lynch

(57) ABSTRACT

A system for use with a balloon disposed at a distal end of an intrabody probe includes an output device, configured to produce an output indicating whether the balloon is elongated, and a processor. The processor is configured to calculate, based on respective locations of multiple elements disposed on a surface of the balloon, multiple values, over an interval, of a parameter indicative of a radius of the balloon. The processor is further configured to modify a state of the output based on at least one of the values. Other embodiments are also described.

21 Claims, 4 Drawing Sheets

(56) References Cited

U.S. PATENT DOCUMENTS

| | | |
|---|---|---|
| 8,456,182 B2 | 6/2013 | Bar-Tal et al. |
| 2016/0220097 A1* | 8/2016 | Ohno ................. A61B 1/00066 |
| 2018/0280080 A1* | 10/2018 | Govari ............... A61B 18/1492 |
| 2019/0350489 A1* | 11/2019 | Ludwin ................. A61B 5/068 |
| 2020/0155224 A1* | 5/2020 | Bar-Tal .............. A61B 18/1492 |
| 2020/0205932 A1* | 7/2020 | Zar ..................... A61B 5/6853 |
| 2021/0077180 A1 | 3/2021 | Govari et al. |
| 2021/0100611 A1 | 4/2021 | Adawi et al. |

\* cited by examiner

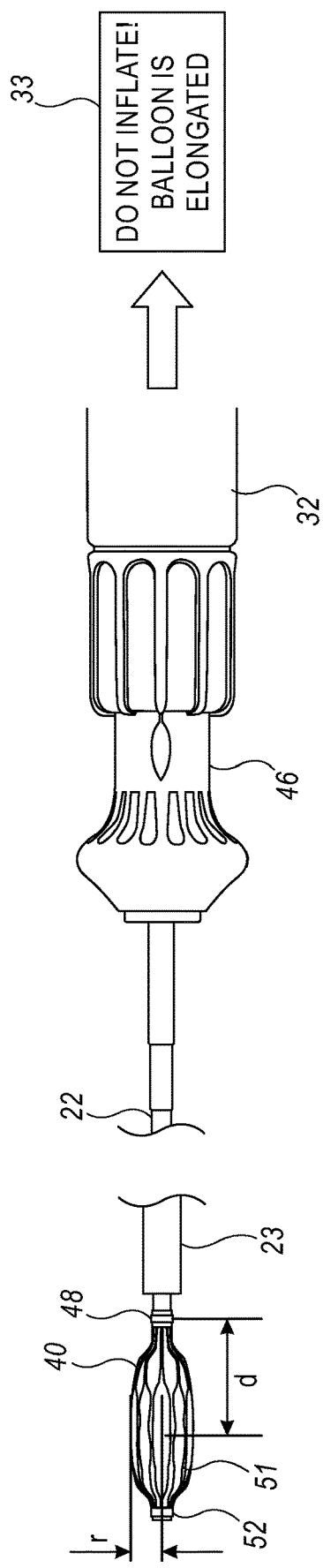
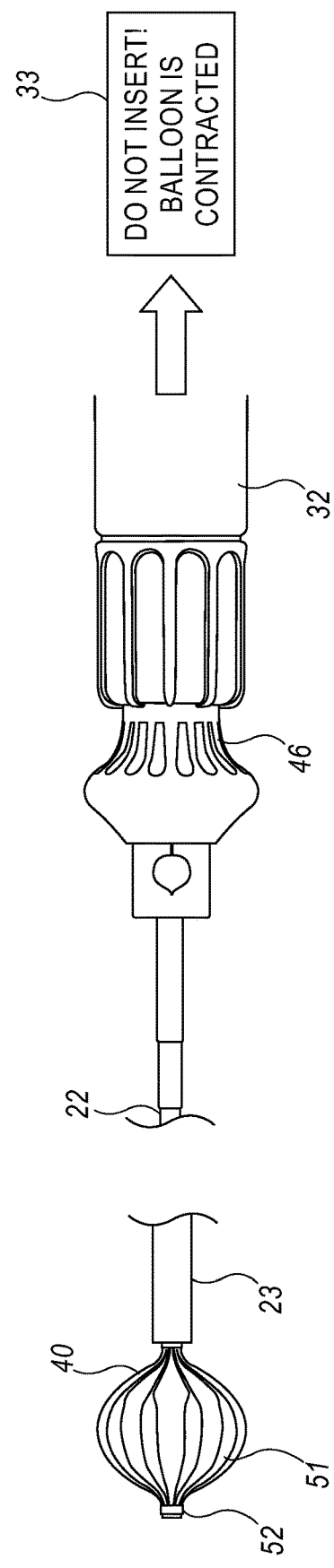
FIG. 2A
FIG. 2B

IDENTIFYING THE STATE OF A BALLOON CATHETER

FIELD OF THE INVENTION

The present invention is related to the field of medical procedures, such as cardiac ablation procedures.

BACKGROUND

US Patent Application Publication 2020/0155224, whose disclosure is incorporated herein by reference, describes an expandable balloon. The balloon is coupled to a distal end of a shaft for insertion into an organ of a patient and includes an expandable membrane, one or more electrodes, and one or more conductive coils configured as magnetic sensors. The electrodes are disposed over an external surface of the membrane, and each of the conductive coils is disposed proximate a respective one of the electrodes.

SUMMARY OF THE INVENTION

There is provided, in accordance with some embodiments of the present invention, a system for use with a balloon disposed at a distal end of an intrabody probe. The system includes an output device, configured to produce an output indicating whether the balloon is elongated, and a processor. The processor is configured to calculate, based on respective locations of multiple elements disposed on a surface of the balloon, multiple values, over an interval, of a parameter indicative of a radius of the balloon. The processor is further configured to modify a state of the output based on at least one of the values.

In some embodiments, the elements include respective electrodes, and the processor is further configured to compute the locations based on respective currents passing through the electrodes or respective voltages at the electrodes.

In some embodiments, the elements include respective coils, and the processor is further configured to compute the locations based on respective currents induced in the coils by a magnetic field.

In some embodiments, the processor is configured to modify the state of the output by:
computing a number based on a difference between the value at an end of the interval and the value at a start of the interval, and
modifying the state of the output in response to the number passing a predefined threshold.

In some embodiments, a duration of the interval is between two and six seconds.

In some embodiments,
the values are radius-related values and the parameter is a radius-related parameter,
the processor is further configured to calculate, based on the locations, multiple distance-related values, over the interval, of a distance-related parameter indicative of a distance between the elements and a portion of the probe proximal to the elements, and
the processor is configured to modify the state of the output based on at least one of the distance-related values.

In some embodiments, the processor is configured to modify the state of the output based on at least one of the distance-related values by:
based on the distance-related values, computing a first change in the distance-related parameter over a first portion of the interval and a second change in the distance-related parameter over a second portion of the interval, and
modifying the state of the output in response to the first change and the second change.

In some embodiments, the processor is configured to modify the state of the output in response to:
the first change and second change having opposite signs, and
respective magnitudes of the first change and second change exceeding a predefined distance-related threshold.

In some embodiments, the processor is further configured to, prior to an end of the interval, cause the output to indicate that the balloon is elongated, and the processor is configured to modify the state of the output by performing an action selected from the group of actions consisting of: modifying the output to indicate that the balloon is no longer elongated, and terminating the output.

In some embodiments, the processor is further configured to:
prior to the end of the interval, inhibit inflation of the balloon, and
based on the at least one of the values, cease to inhibit inflation of the balloon.

In some embodiments, the processor is further configured to, prior to an end of the interval, cause the output to indicate that the balloon is not elongated, and the processor is configured to modify the state of the output by performing an action selected from the group of actions consisting of: modifying the output to indicate that the balloon is elongated, and terminating the output.

There is further provided, in accordance with some embodiments of the present invention, a method for use with a balloon disposed at a distal end of an intrabody probe. The method includes, based on respective locations of multiple elements disposed on a surface of the balloon, calculating multiple values, over an interval, of a parameter indicative of a radius of the balloon. The method further includes, based on at least one of the values, modifying a state of an output indicating whether the balloon is elongated.

There is further provided, in accordance with some embodiments of the present invention, a computer software product including a tangible non-transitory computer-readable medium in which program instructions are stored. The instructions, when read by a processor, cause the processor to calculate, based on respective locations of multiple elements disposed on a surface of a balloon disposed at a distal end of an intrabody probe, multiple values, over an interval, of a parameter indicative of a radius of the balloon. The instructions further cause the processor to modify a state of an output indicating whether the balloon is elongated, based on at least one of the values.

The present invention will be more fully understood from the following detailed description of embodiments thereof, taken together with the drawings, in which:

BRIEF DESCRIPTION OF THE DRAWINGS

FIGS. 2A-B are schematic illustrations of visual outputs generated in response to different respective states of a balloon, in accordance with some embodiments of the present invention;

DETAILED DESCRIPTION OF EMBODIMENTS

Overview

Figure 1:
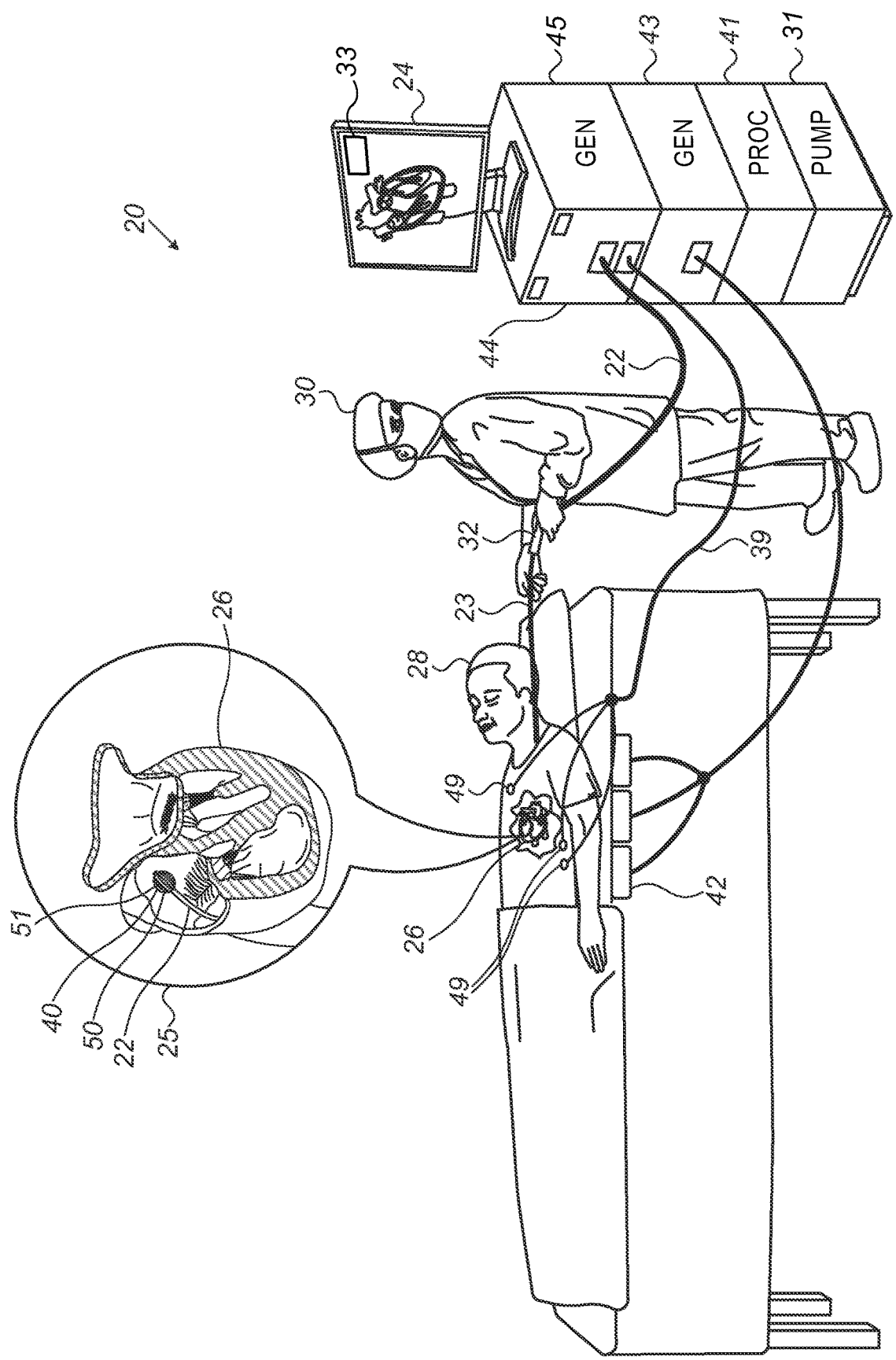
FIG. 1 is a schematic illustration of a system for ablating tissue of a heart of a subject and/or sensing electrogram signals passing through the tissue, in accordance with some embodiments of the present invention.

One type of intrabody medical probe comprises a balloon at its distal end. The surface of the balloon comprises multiple electrodes, which may be used for sensing and/or ablation. Alternatively or additionally, the surface of the balloon may comprise electromagnetic sensors.

To deploy the balloon, the balloon is advanced from the sheath, contracted, and then inflated by a pump. Following usage of the balloon, the balloon is deflated, elongated, and then withdrawn into the sheath.

One challenge, when using such a balloon, is that the user may forget to contract the balloon before inflating the balloon. Similarly, the user may forget to elongate the balloon before attempting to return the balloon into the sheath. In each of these cases, the balloon may be damaged.

To address these challenges, embodiments of the present invention provide a processor configured to track the locations of the electrodes and/or electromagnetic sensors on the balloon. Based on the tracked locations, the processor ascertains whether the balloon is elongated or contracted (i.e., not elongated). In response to ascertaining the state of the balloon, the processor may output any appropriate reminders or warnings, such that the user changes the state of the balloon as required. Alternatively or additionally, the processor may inhibit the pump from inflating the balloon while the balloon is elongated.

For example, following the exiting of the balloon from the sheath, the processor may display a reminder to contract the balloon prior to inflation, and/or disable the pump. Following the contracting of the balloon, the processor may cease displaying the reminder, and/or re-enable the pump.

Similarly, in the event that the user attempts to return the balloon into the sheath before elongating the balloon, the processor may output a reminder to elongate the balloon. Following the elongation, the processor may cease displaying the reminder.

In some embodiments, the processor identifies elongation and contraction events based on changes in the radius of the balloon, which may be derived from the locations of the electrodes and/or sensors on the balloon. For example, one indicator for contraction is an increase in the radius, over an interval of a predefined duration, exceeding a predefined threshold. Similarly, one indicator for elongation is a decrease in the radius, over an interval of a predefined duration, having a magnitude exceeding the predefined threshold.

Alternatively or additionally, the processor may identify elongation and contraction events based on changes in the distance between the electrodes and/or sensors and a more proximal portion of the probe. For example, one indicator for contraction is an increase in the distance over an interval of a predefined duration, immediately followed by a decrease in the distance over another interval of a predefined duration, where the magnitudes of the increase and decrease exceed a predefined threshold. Similarly, one indicator for elongation is a decrease in the distance over an interval of a predefined duration, immediately followed by an increase in the distance over another interval of a predefined duration, where the magnitudes of the decrease and increase exceed the predefined threshold.

System Description

Reference is initially made to FIG. 1, which is a schematic illustration of a system 20 for ablating tissue of a heart 26 of a subject 28 and/or sensing electrogram signals passing through the tissue, in accordance with some embodiments of the present invention.

System 20 comprises an intrabody probe 22. As shown in the inset portion 25 of FIG. 1, probe 22 comprises a balloon 40, which is disposed at the distal end of probe 22. In some embodiments, multiple electrodes 51, which may be used for sensing intracardiac signals and/or ablating cardiac tissue, are disposed on the surface of balloon 40. Alternatively or additionally, multiple coils 50, which are used for electromagnetic sensing, may be disposed on the surface of balloon 40, e.g., as described in US Patent Application Publication 2020/0155224, whose disclosure is incorporated herein by reference.

System 20 further comprises a sheath 23. A physician 30 inserts sheath 23 into the body of subject 28, e.g., via the superior or inferior vena cava of the subject. Subsequently, physician 30 navigates the sheath to a chamber of heart 26. The physician then advances probe 22 through the sheath until the balloon has exited the sheath.

Probe 22 is proximally connected to a pump 31, which may be disposed, for example, within a console 44. Upon the balloon exiting the sheath, physician 30 may cause pump 31 to inflate the balloon by pumping any suitable fluid, such as a saline solution, into the balloon. Subsequently, the balloon may be used to ablate tissue of the chamber. For example, the tissue may be ablated by electric currents passed between pairs of electrodes 51, or between electrodes 51 and another electrode coupled to the subject's chest. Such currents may be generated, for example, by a current generator (GEN) 45. Alternatively or additionally, the balloon may be used to sense signals from the tissue.

System 20 further comprises a processor (PROC) 41, which may be disposed, for example, in console 44. Processor 41 is configured to control pump 31 so as to inflate the balloon, and, in some embodiments, to control current generator 45 so as to ablate the tissue of the subject. In some embodiments, the processor controls the pump and/or current generator in response to control signals generated by the manipulation, by the physician, of buttons, switches, and/or any other control mechanisms on a control handle 32.

In some embodiments, system 20 further comprises a plurality of magnetic-field-generating coils 42. As another current generator 43 passes electric currents through coils 42, the coils generate a magnetic field. This magnetic field induces signals in coils 50 and/or other electromagnetic sensors disposed on probe 22. These signals are carried through the probe to appropriate circuitry (including, for example, analog-to-digital conversion circuitry) in console 44. Processor 41 receives the signals from the circuitry, and, based on the signals, computes the respective locations of the electromagnetic sensors, e.g., as described in U.S. Pat. Nos. 5,391,199, 5,443,489, and 6,788,967 to Ben-Haim, in U.S. Pat. No. 6,690,963 to Ben-Haim et al., in U.S. Pat. No. 5,558,091 to Acker et al., and in U.S. Pat. No. 6,177,792 to Govari, whose respective disclosures are incorporated herein by reference. Based on the locations, the processor may ascertain whether the balloon is elongated or contracted, as described below with reference to the subsequent figures.

Alternatively or additionally, system 20 may comprise multiple reference electrodes 49, which may be coupled to the subject's chest and/or back and connected to console 44 via wires running through a cable 39. Using reference electrodes 49, the processor may compute the locations of one or more electrodes on probe 22, such as electrodes 51 and/or a ring electrode 48 (FIG. 2A), based on respective currents passing through the electrodes or respective voltages at the electrodes. Moreover, the processor may ascertain, for each of the electrodes, whether the electrode is inside or outside sheath 23.

For example, the processor may pass a current through each electrode and measure the resulting voltages between the electrode and the reference electrodes. Alternatively, the processor may apply a voltage between each electrode and the reference electrodes, and measure the resulting currents passing between the electrode and the reference electrodes. Subsequently, the processor may compute the locations based on the measured voltages or currents. (Such embodiments may utilize a location map calibrated using electromagnetic sensors, as described, for example, in U.S. Pat. No. 7,536,218 to Govari et al. and U.S. Pat. No. 8,456,182 to Bar-Tal et al., whose respective disclosures are incorporated herein by reference.) In such embodiments, an increased voltage for a given current applied to an electrode, or a decreased current for a given voltage applied to the electrode, indicates increased impedances between the electrode and the reference electrodes, and thus, may indicate that the electrode has entered sheath 23. Conversely, a decreased voltage or an increased current may indicate that the electrode has exited sheath 23.

Alternatively, for example, the processor may pass currents between the reference electrodes and measure the resulting voltages or currents at the probe electrodes. Subsequently, the processor may compute the locations of the probe electrodes based on the measured voltages or currents, as described, for example, in U.S. Pat. No. 5,983,126 to Wittkampf and U.S. Pat. No. 5,944,022 to Nardella, whose respective disclosures are incorporated herein by reference. In such embodiments, a decreased current through an electrode indicates increased impedances between the electrode and the reference electrodes, and thus, may indicate that the electrode has entered sheath 23. Conversely, an increased current may indicate that the electrode has exited the sheath.

System 20 further comprises at least one output device configured to produce an output indicating whether the balloon is elongated. For example, as further described below with reference to FIGS. 2A-B, a display 24 may display a visual output 33 indicating whether balloon 40 is elongated. Alternatively or additionally, for example, a speaker may output an audio indication as to whether the balloon is elongated.

In general, processor 41 may be embodied as a single processor, or as a cooperatively networked or clustered set of processors. The functionality of processor 41 may be implemented solely in hardware, e.g., using one or more fixed-function or general-purpose integrated circuits, Application-Specific Integrated Circuits (ASICs), and/or Field-Programmable Gate Arrays (FPGAs). Alternatively, this functionality may be implemented at least partly in software. For example, processor 41 may be embodied as a programmed processor comprising, for example, a central processing unit (CPU) and/or a Graphics Processing Unit (GPU). Program code, including software programs, and/or data may be loaded for execution and processing by the CPU and/or GPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Reference is now made to FIGS. 2A-B, which are schematic illustrations of visual outputs 33 generated in response to different respective states of balloon 40, in accordance with some embodiments of the present invention.

In each of FIGS. 2A-B, control handle 32 is shown comprising a knob 46. Knob 46 is connected, via a longitudinal element passing through probe 22, to the distal tip 52 of balloon 40. Thus, when knob 46 is extended as shown in FIG. 2A, distal tip 52 is also extended, such that the balloon is elongated. On the other hand, when knob 46 is retracted as shown in FIG. 2B, distal tip 52 is also retracted, such that the balloon is contracted. Alternatively to knob 46, control handle 32 may comprise any other suitable mechanism for elongating and contracting balloon 40.

While the balloon is within sheath 23, and as the balloon exits the sheath, the balloon is elongated. Thus, as shown in FIG. 2A, upon (and, optionally, prior to) the exiting of the balloon, processor 41 (FIG. 1) may cause output 33 to indicate, to the user, that the balloon is elongated. For example, the output may explicitly indicate that the balloon is elongated. Alternatively or additionally, the output may explicitly indicate that the balloon should not be inflated, thus implicitly indicating that the balloon is elongated. Alternatively or additionally, an audio warning, such as a series of beeps or an extended beep, may implicitly indicate that the balloon is elongated.

Subsequently to (and, optionally, prior to) the exiting of the balloon, the processor repeatedly calculates the value of a radius-related parameter, which is indicative of the radius r of the balloon, based on the respective locations of multiple elements, such as electrodes 51 and/or coils 50 (FIG. 1), disposed on the surface of the balloon. In some embodiments, the radius-related parameter includes the radius, diameter, or circumference of the balloon at the position of the electrodes or coils along the longitudinal axis of the probe. (Typically, the location of each element, as calculated by the processor, is the location of the center of the element.) Such a parameter may be calculated, for example, by fitting a circle to the locations of the elements. In other embodiments, the radius-related parameter includes the average distance between pairs of electrodes 51 (e.g., pairs of opposing electrodes), the average distance between pairs of coils 50 (e.g., pairs of opposing coils), or another parameter derived from one of the aforementioned average distances.

The processor thus continues to calculate values of the radius-related parameter (referred to below as "radius-related values") as the balloon is contracted. Subsequently to the contraction of the balloon, the processor, based on at least one of the radius-related values calculated during a preceding interval, modifies the state of output 33, e.g., by modifying the output to indicate that the balloon is no longer elongated or by simply terminating the output.

For example, the processor may modify the state of the output in response to the most recent radius-related value passing a predefined threshold. (For example, for embodiments in which the radius-related parameter is the radius of the balloon at the position of the electrodes along the longitudinal axis of the probe, the processor may modify the state of the output in response to the most recent radius-related value exceeding the predefined threshold.) Alternatively or additionally, the processor may modify the state of the output in response to another number, which is based on the difference between the radius-related value at the end of the interval and the radius-related value at the start of the interval, passing another predefined threshold. This number may be, for example, the difference itself, or the difference divided by the duration of the interval. For example, the processor may modify the state of the output in response to the difference exceeding the threshold.

In some embodiments, alternatively or additionally to calculating the radius-related values, the processor, based on the respective locations of the elements, repeatedly calculates the value of a distance-related parameter indicative of the distance d between the elements and a portion of the probe, such as ring electrode 48, proximal to the elements. Typically, the distance-related parameter includes the average distance between electrodes 51 and the more proximal portion of the probe or the average distance between coils 50 and the more proximal portion of the probe.

In such embodiments, the processor may modify the state of the output based on at least one of the "distance-related values" calculated during the preceding interval, alternatively or additionally to at least one of the radius-related values. For example, based on the distance-related values, the processor may compute a first change in the distance-related parameter over a first portion of the interval, and a second change in the distance-related parameter over a second portion of the interval. Subsequently, the processor may modify the state of the output in response to the first change and the second change. For example, as further described below with reference to FIG. 3A, the processor may modify the state of the output in response to (i) the first change and second change having opposite signs, and (ii) respective magnitudes of the first change and second change exceeding a predefined threshold.

Alternatively or additionally to displaying output 33 to indicate that the balloon is elongated, the processor may, upon (and, optionally, prior to) the exiting of the balloon from the sheath, inhibit inflation of the balloon. For example, the processor may disable pump 31 (FIG. 1), or simply refrain from activating the pump even if a command to activate the pump is received from physician 30 (FIG. 1). Subsequently, in response to ascertaining, based on at least one of the radius-related and/or distance-related values, that the balloon is contracted, the processor may cease to inhibit inflation of the balloon.

At any time following the contraction of the balloon and prior to the re-elongation of the balloon, the processor may cause output 33 to indicate that the balloon is contracted, as shown in FIG. 2B. For example, the processor may cause the output to indicate that the balloon is contracted in response to ascertaining that the balloon is contracted, in response to ascertaining that the balloon was or is being deflated, or in response to ascertaining (e.g., based on an increase in impedance) that a more proximal portion of the probe, such as ring electrode 48, entered the sheath before the balloon was re-elongated, as shown in FIG. 2B.

Output 33 may explicitly indicate that the balloon is contracted. Alternatively or additionally, the output may explicitly indicate that the balloon should not be inserted into the sheath, thus implicitly indicating that the balloon is contracted. Alternatively or additionally, an audio warning, such as a series of beeps or an extended beep, may implicitly indicate that the balloon is contracted.

In addition, subsequently to the contraction of the balloon, the processor continues to repeatedly calculate the value of the radius-related parameter and/or the value of the distance-related parameter. The processor thus continues to calculate the radius-related values and/or distance-related values as the balloon is re-elongated. Subsequently to the re-elongation of the balloon, the processor, based on at least one of the radius-related values and/or distance-related values calculated during a preceding interval, modifies the state of output 33, e.g., by modifying the output to indicate that the balloon is elongated or by simply terminating the output.

For example, the processor may modify the state of the output in response to the most recent radius-related value passing a predefined threshold. (For example, for embodiments in which the radius-related parameter is the radius of the balloon at the position of the electrodes along the longitudinal axis of the probe, the processor may modify the state of the output in response to the most recent radius-related value being less than the predefined threshold.) Alternatively or additionally, the processor may modify the state of the output in response to another number, which is based on the difference between the radius-related value at the end of the interval and the radius-related value at the start of the interval, passing another predefined threshold. For example, the processor may modify the state of the output in response to the negative of the difference (optionally divided by the duration of the interval) exceeding a predefined positive threshold.

Alternatively or additionally, the processor may modify the state of the output in response to a first change, over a first portion of the interval, and a second change, over a second portion of the interval, in the distance-related parameter. For example, as further described below with reference to FIG. 3B, the processor may modify the state of the output in response to (i) the first change and second change having opposite signs, and (ii) respective magnitudes of the first change and second change exceeding a predefined threshold.

In some embodiments, a user, using any suitable input interface (such as a touch screen belonging to display 24 (FIG. 1)), may overrule the computer-implemented logic for modifying the state of output 33. Thus, for example, in response to receiving an input indicating that the balloon is in a particular state, the processor may terminate an output indicating that the balloon is in the other state.

Example Algorithms

Figure 3A:
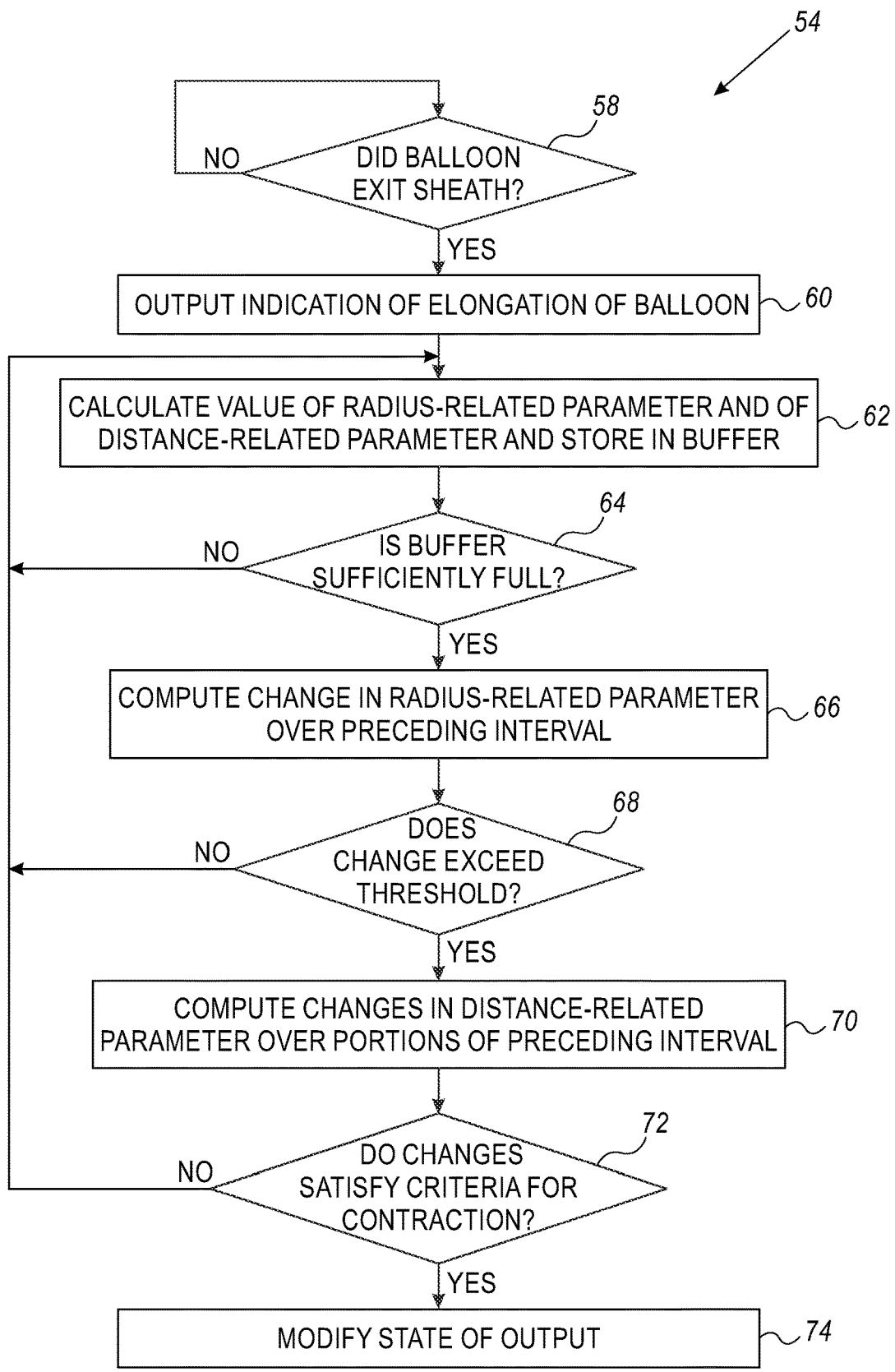
FIG. 3A is a flow diagram for an algorithm for facilitating inflation of a balloon, in accordance with some embodiments of the present invention.

Reference is now made to FIG. 3A, which is a flow diagram for an algorithm 54 for facilitating inflation of balloon 40 (FIG. 1), in accordance with some embodiments of the present invention. Algorithm 54 is executed by processor 41 prior to and during the deployment of balloon 40.

At the start of algorithm 54, the processor repeatedly checks, at a checking step 58, whether the balloon exited the sheath. For example, the processor may check for a drop in the impedances between electrodes 51 and reference electrodes 49 (FIG. 1) and in the impedances between ring electrode 48 (FIG. 2A) and reference electrodes 49. Alternatively, the processor may check only for a drop in the impedances between ring electrode 48 and reference electrodes 49.

In response to ascertaining that the balloon has exited the sheath, the processor, at an outputting step 60, outputs an indication that the balloon is elongated, e.g., as described above with reference to FIG. 2A.

In other embodiments, outputting step 60 is performed even before the balloon fully exits the sheath. For example, the processor may perform outputting step 60 in response to ascertaining that the electrodes and/or sensors on the balloon have exited the sheath, or upon the insertion of the probe into the sheath. (In such embodiments, checking step 58 need not necessarily be performed.)

Subsequently to performing outputting step 60, the processor repeatedly performs a calculating step 62, at which the processor calculates the value of the radius-related parameter and of the distance-related parameter. (As described above with reference to the previous figures, this calculation is based on the respective locations of multiple elements, such as electrodes 51 and/or coils 50, disposed on the surface of the balloon.) Each calculated parameter value is stored in a buffer.

Subsequently to each performance of calculating step 62, the processor checks, at another checking step 64, whether the buffer is sufficiently full. In particular, the processor checks whether the values in the buffer span an interval of a predefined duration T, where T may be between two and six seconds, for example. If the buffer is not sufficiently full, the processor returns to calculating step 62.

Upon ascertaining that the buffer is sufficiently full, the processor, at a change-computing step 66, computes a change in the radius-related parameter over the interval. For example, the processor may compute $r[N]-r[N-kT]$, where $r[N]$ is the most-recently calculated value of the radius, k is the number of values calculated per second (i.e., the number of times per second that calculating step 62 is performed), and T is the duration of the interval in seconds. (In the event that kT is not an integer, kT may be rounded to the nearest integer.)

Subsequently to calculating the change, the processor checks, at another checking step 68, whether the change exceeds a predefined threshold $t_r$. (For embodiments in which the radius-related parameter is the radius of the balloon, $t_r$ may be, for example, between 1 and 5 mm.) If not, the processor returns to calculating step 62. Otherwise, the processor, at another change-computing step 70, computes respective changes in the distance-related parameter over two portions of the preceding interval, whose respective durations may be equal or unequal to one another. For example, the processor may compute the changes in the distance over the two halves of the preceding interval, i.e., $d[N-kT/2]-d[N-kT]$ and $d[N]-d[N-kT/2]$, where $d[N]$ is the most-recently calculated value of the distance. Subsequently, the processor checks, at another checking step 72, whether the changes satisfy predefined criteria so as to indicate contraction of the balloon.

For example, the inventors have observed that during contraction of the balloon, the distance increases and then decreases back to its initial value (approximately). The processor may therefore check whether (i) $d[N-kT/2]-d[N-kT]>t_d$ and (ii) $d[N]-d[N-kT/2]<-t_d$, where $t_d$ is a predefined threshold. ($t_d$ may be between 0.5 and 3 mm, for example.) In other words, the processor may check whether $d[N-kT/2]-d[N-kT]$ is positive, $d[N]-d[N-kT/2]$ is negative, and both $|d[N-kT/2]-d[N-kT]|$ and $|d[N]-d[N-kT/2]|$ are greater than $t_d$.

In response to ascertaining that the changes satisfy the criteria, the processor modifies the state of the output at an output-modifying step 74, e.g., as described above with reference to FIG. 2A. Optionally, the processor may also cease inhibiting inflation of the balloon; for example, the processor may re-enable the pump. If, on the other hand, the changes do not satisfy the criteria, the processor returns to calculating step 62.

In other embodiments, the iterative performance of calculating step 62 begins even before the balloon exits the sheath. Alternatively or additionally, change-computing step 70 and checking step 72 may be performed before change-computing step 66; in particular, change-computing step 66 may be performed in response to ascertaining, at checking step 72, that the changes in the distance-related parameter satisfy the criteria.

Figure 3B:
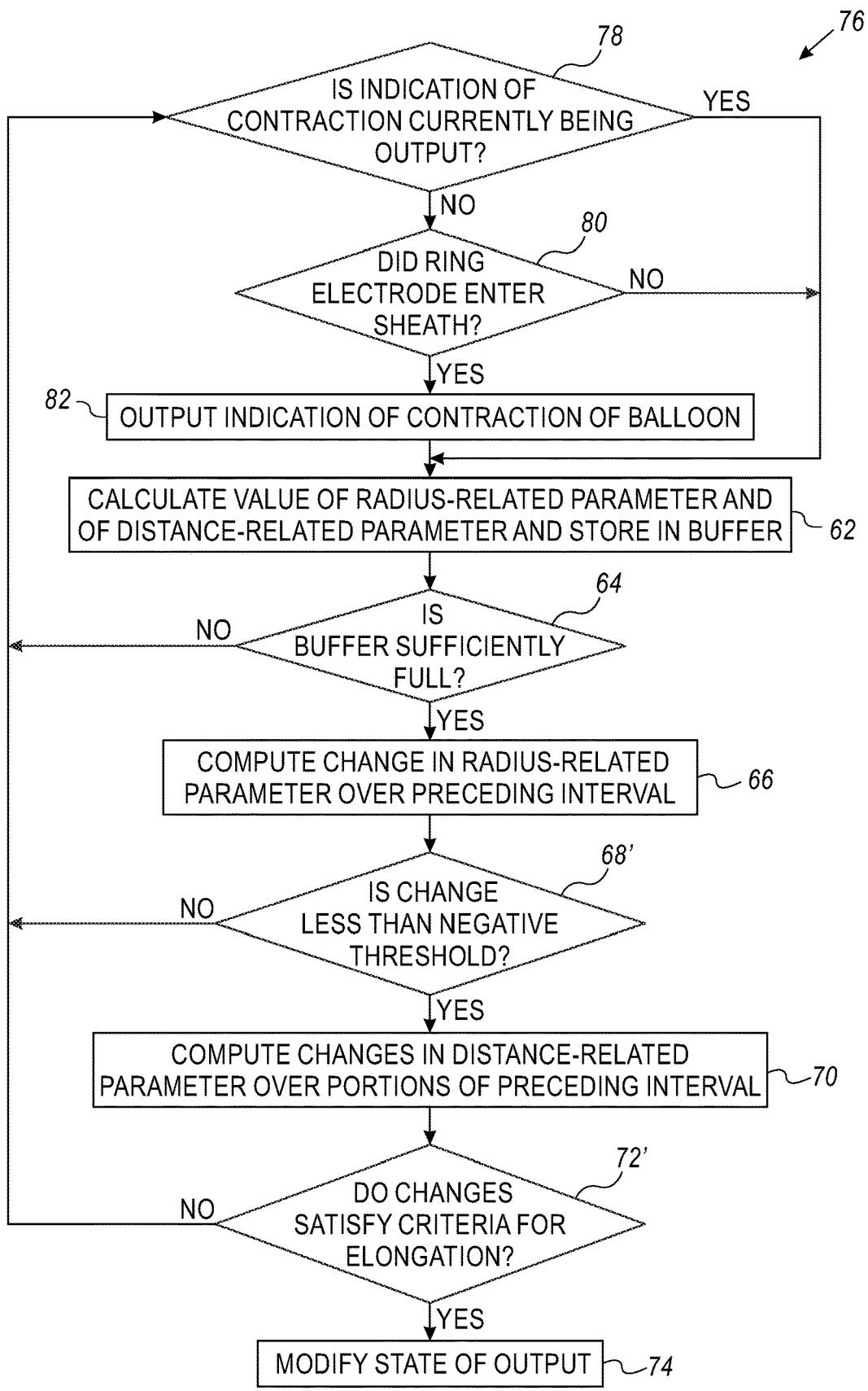
FIG. 3B is a flow diagram for an algorithm for facilitating re-elongation of a balloon, in accordance with some embodiments of the present invention.

Reference is now made to FIG. 3B, which is a flow diagram for an algorithm 76 for facilitating re-elongation of balloon 40 (FIG. 1), in accordance with some embodiments of the present invention. Algorithm 76 may be executed by processor 41 at any time following the contraction of the balloon.

Algorithm 76 begins with a checking step 78, at which the processor checks whether an indication of contraction of the balloon is currently being output. If yes, the processor proceeds to calculating step 62. Otherwise, the processor checks, at another checking step 80, whether ring electrode 48 (FIG. 2A) entered the sheath. If yes, the processor, at an outputting step 82, outputs an indication that the balloon is contracted, e.g., as described above with reference to FIG. 2B. Subsequently, or if the ring electrode did not yet enter the sheath, the processor proceeds to calculating step 62.

Following each performance of calculating step 62, the processor performs checking step 64, as described above with reference to FIG. 3A. If the buffer is not sufficiently full, the processor returns to checking step 78. Otherwise, the processor performs change-computing step 66, as described above with reference to FIG. 3A. Subsequently, the processor checks, at another checking step 68', whether the change is less than a negative threshold. For example, the processor may check whether $r[N]-r[N-kT]$ is less than $-t_r$. If not, the processor returns to checking step 78. Otherwise, the processor proceeds to change-computing step 70.

Subsequently to performing change-computing step 70, the processor checks, at another checking step 72', whether the changes satisfy predefined criteria so as to indicate elongation of the balloon. For example, the inventors have observed that during elongation of the balloon, the distance-related parameter decreases and then increases back to its initial value (approximately). The processor may therefore check whether (i) $d[N-kT/2]-d[N-kT]<-t_d$ and (ii) $d[N]-d[N-kT/2]>t_d$. In other words, the processor may check whether $d[N-kT/2]-d[N-kT]$ is negative, $d[N]-d[N-kT/2]$ is positive, and both $|d[N-kT/2]-d[N-kT]|$ and $|d[N]-d[N-kT/2]|$ are greater than $t_d$.

(Although the examples above assume that algorithm 76 uses the same predefined interval duration T as does algorithm 54 (FIG. 3A), it is noted that algorithm 76 may use a different interval duration.)

If the changes satisfy the predefined criteria, the processor modifies the state of the output at output-modifying step 74, e.g., as described above with reference to FIG. 2B. Otherwise, the processor returns to checking step 78.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for use with a balloon disposed at a distal end of an intrabody probe, the system comprising:
   an output device, configured to produce an output indicating whether the balloon is elongated; and
   a processor, configured to:
      based on respective locations of multiple elements disposed on a surface of the balloon, calculate multiple values, over an interval, of a parameter indicative of a radius of the balloon;
      compute a number based on a difference between at least one value of the multiple values at a start of the interval and the at least one value at an end of the interval; and
      based on at least the difference passing a predefined threshold, modify a state of the output.

2. The system according to claim 1, wherein the elements include respective electrodes, and wherein the processor is further configured to compute the locations based on respective currents passing through the electrodes or respective voltages at the electrodes.

3. The system according to claim 1, wherein the elements include respective coils, and wherein the processor is further configured to compute the locations based on respective currents induced in the coils by a magnetic field.

4. The system according to claim 1, wherein a duration of the interval is between two and six seconds.

5. The system according to claim 1,
   wherein the values are radius-related values and the parameter is a radius-related parameter,
   wherein the processor is further configured to calculate, based on the locations, multiple distance-related values, over the interval, of a distance-related parameter indicative of a distance between the elements and a portion of the probe proximal to the elements, and
   wherein the processor is further configured to modify the state of the output based on at least one of the distance-related values.

6. The system according to claim 5, wherein the processor is configured to modify the state of the output based on at least one of the distance-related values by:
   based on the distance-related values, computing a first change in the distance-related parameter over a first portion of the interval and a second change in the distance-related parameter over a second portion of the interval, and
   modifying the state of the output in response to the first change and the second change.

7. The system according to claim 6, wherein the processor is configured to modify the state of the output in response to:
   the first change and second change having opposite signs, and
   respective magnitudes of the first change and second change exceeding a predefined distance-related threshold.

8. The system according to claim 1, wherein the processor is further configured to, prior to an end of the interval, cause the output to indicate that the balloon is elongated, and wherein the processor is configured to modify the state of the output by performing an action selected from the group of actions consisting of: modifying the output to indicate that the balloon is no longer elongated, and terminating the output.

9. The system according to claim 8, wherein the processor is further configured to:
   prior to the end of the interval, inhibit inflation of the balloon, and
   based on the at least one of the values, cease to inhibit inflation of the balloon.

10. The system according to claim 1, wherein the processor is further configured to, prior to an end of the interval, cause the output to indicate that the balloon is not elongated, and wherein the processor is configured to modify the state of the output by performing an action selected from the group of actions consisting of: modifying the output to indicate that the balloon is elongated, and terminating the output.

11. A method for use with a balloon disposed at a distal end of an intrabody probe, the method comprising:
   based on respective locations of multiple elements disposed on a surface of the balloon, calculating multiple values, over an interval, of a parameter indicative of a radius of the balloon;
   computing a number based on a difference between at least one value of the multiple values at a start of the interval and the at least one value at an end of the interval; and
   based on at least the difference passing a predefined threshold, modifying a state of an output indicating whether the balloon is elongated.

12. The method according to claim 11, wherein the elements include respective electrodes, and wherein the method further comprises computing the locations based on respective currents passing through the electrodes or respective voltages at the electrodes.

13. The method according to claim 11, wherein the elements include respective coils, and wherein the method further comprises computing the locations based on respective currents induced in the coils by a magnetic field.

14. The method according to claim 11, wherein a duration of the interval is between two and six seconds.

15. The method according to claim 11,
   wherein the values are radius-related values and the parameter is a radius-related parameter,
   wherein the method further comprises, based on the locations, calculating multiple distance-related values, over the interval, of a distance-related parameter indicative of a distance between the elements and a portion of the probe proximal to the elements, and
   wherein modifying the state of the output further comprises modifying the state of the output based on at least one of the distance-related values.

16. The method according to claim 15, wherein modifying the state of the output based on at least one of the distance-related values further comprises:
   based on the distance-related values, computing a first change in the distance-related parameter over a first portion of the interval and a second change in the distance-related parameter over a second portion of the interval, and
   modifying the state of the output in response to the first change and the second change.

17. The method according to claim 16, wherein modifying the state of the output in response to the first change and the second change comprises modifying the state of the output in response to:

the first change and second change having opposite signs, and respective magnitudes of the first change and second change exceeding a predefined distance-related threshold.

18. The method according to claim 11, further comprising, prior to an end of the interval, causing the output to indicate that the balloon is elongated, wherein modifying the state of the output comprises performing an action selected from the group of actions consisting of:

modifying the output to indicate that the balloon is no longer elongated, and terminating the output.

19. The method according to claim 18, further comprising:

prior to the end of the interval, inhibiting inflation of the balloon; and based on the at least one of the values, ceasing to inhibit inflation of the balloon.

20. The method according to claim 11, further comprising, prior to an end of the interval, causing the output to indicate that the balloon is not elongated, wherein modifying the state of the output comprises performing an action selected from the group of actions consisting of: modifying the output to indicate that the balloon is elongated, and terminating the output.

21. A computer software product comprising a tangible non-transitory computer-readable medium in which program instructions are stored, which instructions, when read by a processor, cause the processor to:

based on respective locations of multiple elements disposed on a surface of a balloon disposed at a distal end of an intrabody probe, calculate multiple values, over an interval, of a parameter indicative of a radius of the balloon, compute a number based on a difference between at least one value of the multiple values at a start of the interval and the at least one value at an end of the interval, and based on at least the difference passing a predefined threshold, modify a state of an output indicating whether the balloon is elongated.

* * * * *